US012661490B2

(12) United States Patent
Schreck

(10) Patent No.: US 12,661,490 B2
(45) Date of Patent: Jun. 23, 2026

(54) DEVICES FOR SHUNTING BLOOD

(71) Applicant: Inspire M.D Ltd., Tel Aviv (IL)

(72) Inventor: Stefan Schreck, Duvall, WA (US)

(73) Assignee: Inspire M.D Ltd., Tel Aviv (IL)

( * ) Notice: Subject to any disclaimer, the term of this patent is extended or adjusted under 35 U.S.C. 154(b) by 673 days.

(21) Appl. No.: 17/889,423

(22) Filed: Aug. 17, 2022

(65) Prior Publication Data

US 2024/0058591 A1 Feb. 22, 2024

(51) Int. Cl.
A61M 39/06 (2006.01)
A61M 29/02 (2006.01)
(Continued)

(52) U.S. Cl.
CPC ........ A61M 39/0613 (2013.01); A61M 29/02 (2013.01); A61M 39/0208 (2013.01);
(Continued)

(58) Field of Classification Search
CPC .............. A61M 39/0613; A61M 29/02; A61M 39/0208; A61M 39/1011; A61M 2029/025; A61M 2039/0241; A61M 2039/0258; A61M 2039/062; A61M 25/0662; A61M 2025/0681; A61M 25/0097; A61M 39/06; A61M 25/007; A61M 25/003; A61B 1/00135
See application file for complete search history.

(56) References Cited

U.S. PATENT DOCUMENTS 3,641,994 A 2/1972 Gosling et al.
3,889,687 A 6/1975 Harris et al.
(Continued)

FOREIGN PATENT DOCUMENTS

AU 774994 B2 7/2004
CN 100534392 C 9/2009
(Continued)

OTHER PUBLICATIONS

"International Standard, ISO 80368-7: Small-bore connectors for liquids and gases in healthcare applications—Part 7: Connectors for intravascular or hypodermic applications, Oct. 15, 2016, ISO, p. iv-11, https://simplestmedical.com/wp-content/uploads/2022/12/ISO-80369-7-2016-.pdf" (Year: 2016).*
(Continued)

*Primary Examiner* — Rebecca E Eisenberg
*Assistant Examiner* — Katherine-Ph Minh Pham
(74) *Attorney, Agent, or Firm* — Meitar Patents LTD.; Daniel Kligler

(57) ABSTRACT
An apparatus includes a hub including a front port, a side port, and a back port including a hemostasis valve. The apparatus further includes a sheath extending from the hemostasis valve through the front port and shaped to define one or more lateral openings within the hub. The sheath is configured for insertion into a blood vessel such that, subsequently to the insertion, a rate of flow of blood between the side port and the blood vessel via the lateral openings is controllable using an instrument passing through the hemostasis valve and into the sheath such that the instrument closes at least a portion of the lateral openings. Other embodiments are also described.

22 Claims, 5 Drawing Sheets

(51) Int. Cl.
    *A61M 39/02*       (2006.01)
    *A61M 39/10*       (2006.01)

(52) U.S. Cl.
    CPC ... *A61M 39/1011* (2013.01); *A61M 2029/025*
    (2013.01); *A61M 2039/0241* (2013.01); *A61M*
    *2039/0258* (2013.01); *A61M 2039/062*
    (2013.01)

(56) References Cited

U.S. PATENT DOCUMENTS

| | | | |
|---|---|---|---|
| 4,559,034 A | 12/1985 | Kirita et al. | |
| 4,661,097 A | 4/1987 | Fischell et al. | |
| 4,874,359 A | 10/1989 | White et al. | |
| 5,334,163 A | 8/1994 | Sinnett | |
| 5,374,239 A | 12/1994 | Mischenko | |
| 5,395,105 A | 3/1995 | Thommen, Jr. | |
| 5,437,290 A | 8/1995 | Bolger et al. | |
| 5,601,572 A | 2/1997 | Middleman et al. | |
| 5,843,244 A | 12/1998 | Pelton et al. | |
| 5,954,691 A | 9/1999 | Prosl | |
| 6,019,772 A | 2/2000 | Shefaram et al. | |
| 6,019,778 A | 2/2000 | Wilson et al. | |
| 6,071,269 A | 6/2000 | Schnell et al. | |
| 6,109,406 A | 8/2000 | Takagi et al. | |
| 6,129,755 A | 10/2000 | Mathis et al. | |
| 6,206,868 B1 | 3/2001 | Parodi | |
| 6,235,042 B1 | 5/2001 | Katzman | |
| 6,295,989 B1 | 10/2001 | Connors, III | |
| 6,312,454 B1 | 11/2001 | Stoeckel et al. | |
| 6,312,455 B2 | 11/2001 | Duerig et al. | |
| 6,413,235 B1 | 7/2002 | Parodi | |
| 6,423,032 B2 | 7/2002 | Parodi | |
| 6,425,898 B1 | 7/2002 | Wilson et al. | |
| 6,503,271 B2 | 1/2003 | Duerig et al. | |
| 6,514,236 B1 * | 2/2003 | Stratienko | A61M 25/0041 |
| | | | 604/513 |
| 6,540,712 B1 | 4/2003 | Parodi et al. | |
| 6,582,396 B1 | 6/2003 | Parodi | |
| 6,632,236 B2 | 10/2003 | Hogendijk | |
| 6,641,573 B1 | 11/2003 | Parodi | |
| 6,645,222 B1 | 11/2003 | Parodi et al. | |
| 6,682,505 B2 | 1/2004 | Bates et al. | |
| 6,689,084 B2 | 2/2004 | Kaganov et al. | |
| 6,726,659 B1 * | 4/2004 | Stocking | A61M 25/0693 |
| | | | 604/164.01 |
| 6,743,219 B1 | 6/2004 | Dwyer et al. | |
| 6,773,446 B1 | 8/2004 | Dwyer et al. | |
| 6,859,986 B2 | 3/2005 | Jackson et al. | |
| 6,863,685 B2 | 3/2005 | Davila et al. | |
| 6,905,490 B2 | 6/2005 | Parodi | |
| 6,908,474 B2 | 6/2005 | Hogendijk et al. | |
| 6,935,404 B2 | 8/2005 | Duerig et al. | |
| 6,936,060 B2 | 8/2005 | Hogendijk et al. | |
| 6,942,688 B2 | 9/2005 | Bartholf et al. | |
| 7,063,685 B2 | 6/2006 | Rome | |
| 7,344,527 B2 | 3/2008 | Schweikert et al. | |
| 7,879,011 B2 | 2/2011 | Chang | |
| 7,927,347 B2 | 4/2011 | Hogendijk et al. | |
| 7,998,104 B2 | 8/2011 | Chang | |
| 8,002,728 B2 | 8/2011 | Chang | |
| 8,157,760 B2 | 4/2012 | Criado et al. | |
| 8,235,943 B2 | 8/2012 | Breznock et al. | |
| 8,308,709 B2 | 11/2012 | Chang | |
| 8,343,089 B2 | 1/2013 | Chang | |
| 8,414,516 B2 | 4/2013 | Chang | |
| 8,444,586 B2 | 5/2013 | Beck | |
| 8,545,432 B2 | 10/2013 | Renati et al. | |
| 8,545,552 B2 | 10/2013 | Garrison et al. | |
| 8,574,245 B2 | 11/2013 | Garrison et al. | |
| 8,740,834 B2 | 6/2014 | Criado et al. | |
| 8,784,355 B2 | 7/2014 | Criado et al. | |
| 8,858,490 B2 | 10/2014 | Chou et al. | |
| 8,870,805 B2 | 10/2014 | Chang | |
| 9,011,364 B2 | 4/2015 | Criado et al. | |

| | | | |
|---|---|---|---|
| 9,011,467 B2 | 4/2015 | Garrison et al. | |
| 9,084,857 B2 | 7/2015 | Cully et al. | |
| 9,126,018 B1 | 9/2015 | Garrison | |
| 9,138,527 B2 | 9/2015 | Renati et al. | |
| 9,179,909 B2 | 11/2015 | Garrison et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,295,817 B2 | 3/2016 | Chang | |
| 9,399,118 B2 | 7/2016 | Kume et al. | |
| 9,427,305 B2 | 8/2016 | Kuraguntla et al. | |
| 9,492,637 B2 | 11/2016 | Garrison et al. | |
| 9,526,504 B2 | 12/2016 | Chang | |
| 9,561,345 B2 | 2/2017 | Garrison et al. | |
| 9,623,228 B2 | 4/2017 | Ryan et al. | |
| 9,655,755 B2 | 5/2017 | Chou et al. | |
| 9,662,118 B2 | 5/2017 | Chang | |
| 9,662,480 B2 | 5/2017 | Kume et al. | |
| 9,668,743 B2 | 6/2017 | Cully et al. | |
| 9,669,183 B2 | 6/2017 | Chang | |
| 9,669,191 B2 | 6/2017 | Chou et al. | |
| 9,693,789 B2 | 7/2017 | Garrison et al. | |
| 9,789,242 B2 | 10/2017 | Criado et al. | |
| 9,820,761 B2 | 11/2017 | Garrison et al. | |
| 9,833,555 B2 | 12/2017 | Criado et al. | |
| 9,861,783 B2 | 1/2018 | Garrison et al. | |
| 10,039,906 B2 | 8/2018 | Kume et al. | |
| 10,085,864 B2 | 10/2018 | Chou et al. | |
| 10,159,479 B2 | 12/2018 | Hentges et al. | |
| 10,182,801 B2 | 1/2019 | Garrison | |
| 10,188,399 B2 | 1/2019 | Chang | |
| 10,226,563 B2 | 3/2019 | Garrison et al. | |
| 10,226,598 B2 | 3/2019 | Chou et al. | |
| 10,238,853 B2 | 3/2019 | Kume et al. | |
| 10,272,269 B2 | 4/2019 | Garrison et al. | |
| 10,286,139 B2 | 5/2019 | Criado et al. | |
| 10,327,790 B2 | 6/2019 | Garrison et al. | |
| 10,328,232 B2 | 6/2019 | Chang | |
| 10,357,242 B2 | 7/2019 | Garrison et al. | |
| 10,369,346 B2 | 8/2019 | Ryan et al. | |
| 10,384,034 B2 | 8/2019 | Garrison et al. | |
| 10,390,847 B2 | 8/2019 | Garrison et al. | |
| 10,426,497 B2 | 10/2019 | Chou et al. | |
| 10,426,885 B2 | 10/2019 | Criado et al. | |
| 10,485,917 B2 | 11/2019 | Criado et al. | |
| 10,543,307 B2 | 1/2020 | Criado et al. | |
| 10,709,832 B2 | 7/2020 | Criado et al. | |
| 10,722,239 B2 | 7/2020 | Chang | |
| 10,779,835 B2 | 9/2020 | Chang | |
| 10,779,855 B2 | 9/2020 | Garrison | |
| 10,799,244 B2 | 10/2020 | Cully et al. | |
| 10,799,669 B2 | 10/2020 | Chou et al. | |
| 10,828,460 B2 | 11/2020 | Chang | |
| 10,864,357 B2 | 12/2020 | Kume et al. | |
| 10,881,393 B2 | 1/2021 | Hentges et al. | |
| 10,918,504 B2 | 2/2021 | Wallace et al. | |
| 10,925,709 B2 | 2/2021 | Rogers et al. | |
| 10,939,929 B2 | 3/2021 | Garrison et al. | |
| 10,952,882 B2 | 3/2021 | Chou et al. | |
| 10,973,502 B2 | 4/2021 | Garrison | |
| 11,020,133 B2 | 6/2021 | Wilson et al. | |
| 11,027,104 B2 | 6/2021 | Kume et al. | |
| 11,097,132 B2 | 8/2021 | Garrison et al. | |
| 11,103,627 B2 | 8/2021 | Garrison et al. | |
| 11,129,965 B2 | 9/2021 | Humbert et al. | |
| 11,141,259 B2 | 10/2021 | MacDonald et al. | |
| 11,364,369 B2 | 6/2022 | Chou et al. | |
| 11,478,248 B2 | 10/2022 | Sultan et al. | |
| 12,156,960 B2 | 12/2024 | Chou et al. | |
| 12,156,961 B2 | 12/2024 | Kume et al. | |
| 2001/0047184 A1 | 11/2001 | Connors, III | |
| 2002/0087119 A1 | 7/2002 | Parodi | |
| 2004/0073243 A1 | 4/2004 | Sepetka | |
| 2005/0113798 A1 * | 5/2005 | Slater | A61M 25/10 |
| | | | 606/213 |
| 2007/0055296 A1 | 3/2007 | Stergiopulos | |
| 2009/0024072 A1 | 1/2009 | Criado et al. | |
| 2009/0048654 A1 | 2/2009 | Chmura et al. | |
| 2009/0240235 A1 | 9/2009 | Murata | |

(56) References Cited

U.S. PATENT DOCUMENTS

| | | | |
|---|---|---|---|
| 2010/0168682 A1 | 7/2010 | Braga et al. | |
| 2010/0198158 A1 | 8/2010 | Loewen | |
| 2010/0204684 A1 | 8/2010 | Garrison et al. | |
| 2011/0004147 A1 | 1/2011 | Renati et al. | |
| 2011/0098649 A1 | 4/2011 | Nardeo et al. | |
| 2011/0251482 A1 | 10/2011 | Kellerman et al. | |
| 2011/0284776 A1 | 11/2011 | Gay et al. | |
| 2012/0046515 A1 | 2/2012 | Woo et al. | |
| 2013/0041305 A1 | 2/2013 | Tarlian, Jr. et al. | |
| 2013/0317409 A1 | 11/2013 | Cully et al. | |
| 2014/0031854 A1 | 1/2014 | Goode et al. | |
| 2014/0074144 A1 | 3/2014 | Shrivastava et al. | |
| 2014/0088482 A1 | 3/2014 | Schlaeper et al. | |
| 2014/0221932 A1 | 8/2014 | Puhasmagi et al. | |
| 2014/0243759 A1 | 8/2014 | Yoon et al. | |
| 2014/0296769 A1 | 10/2014 | Hyde et al. | |
| 2014/0303427 A1 | 10/2014 | Kerkhoffs et al. | |
| 2016/0022292 A1 | 1/2016 | Stigall et al. | |
| 2016/0220791 A1* | 8/2016 | Akcay | A61B 5/150732 |
| 2016/0242764 A1 | 8/2016 | Garrison et al. | |
| 2016/0296690 A1* | 10/2016 | Kume | A61M 1/3613 |
| 2016/0317288 A1 | 11/2016 | Rogers et al. | |
| 2016/0354082 A1 | 12/2016 | Oz et al. | |
| 2017/0056175 A1 | 3/2017 | Chin et al. | |
| 2019/0125512 A1* | 5/2019 | MacDonald | A61B 17/34 |
| 2019/0328411 A1 | 10/2019 | Vale et al. | |
| 2019/0344058 A1 | 11/2019 | Hakim | |
| 2019/0351182 A1 | 11/2019 | Chou et al. | |
| 2019/0358443 A1 | 11/2019 | Lopez et al. | |
| 2019/0380563 A1* | 12/2019 | Sanghvi | A61M 25/0662 |
| 2020/0289039 A1 | 9/2020 | Bullington et al. | |
| 2020/0289794 A1 | 9/2020 | Fantuzzi | |
| 2020/0292367 A1 | 9/2020 | Elizalde | |
| 2020/0397472 A1 | 12/2020 | MacDonald et al. | |
| 2021/0001091 A1* | 1/2021 | Schmidt | A61M 29/00 |
| 2021/0145453 A1 | 5/2021 | Kume | |
| 2021/0298929 A1 | 9/2021 | Wallace et al. | |
| 2022/0201081 A1 | 6/2022 | Nagamura | |
| 2022/0226556 A1 | 7/2022 | Drake et al. | |
| 2023/0013548 A1 | 1/2023 | Vale et al. | |
| 2023/0097442 A1 | 3/2023 | Criado et al. | |
| 2024/0197349 A1 | 6/2024 | Kelly et al. | |
| 2024/0423626 A1 | 12/2024 | Chang | |
| 2024/0424266 A1 | 12/2024 | Kume et al. | |
| 2025/0114506 A1 | 4/2025 | Chou et al. | |
| 2025/0114507 A1 | 4/2025 | Garrison et al. | |
| 2025/0114586 A1 | 4/2025 | Ryan et al. | |
| 2025/0127975 A1 | 4/2025 | Kume et al. | |

FOREIGN PATENT DOCUMENTS

| | | |
|---|---|---|
| CN | 204709643 U | 10/2015 |
| CN | 209848141 U | 12/2019 |
| EP | 2497520 A1 | 9/2012 |
| EP | 1356836 B1 | 11/2013 |
| JP | S51115963 U | 9/1976 |
| JP | S5542266 Y2 | 10/1980 |
| JP | S6025136 B2 | 6/1985 |
| JP | S60100958 A | 6/1985 |
| JP | S62501057 A | 4/1987 |
| JP | S6223488 U | 6/1987 |
| JP | H065636 U | 1/1994 |
| JP | H09-507148 A | 7/1997 |
| JP | 2014-526306 A | 10/2014 |
| JP | 2019154669 A | 9/2019 |
| JP | 2019524346 A | 9/2019 |
| JP | 2020142074 A | 9/2020 |
| PT | 1951362 E | 3/2010 |
| RU | 2759406 C1 | 11/2021 |
| WO | 1995018647 A2 | 7/1995 |
| WO | 2004011058 A2 | 2/2004 |
| WO | 2004058321 A2 | 7/2004 |
| WO | 2005051206 A1 | 6/2005 |
| WO | 2007078680 A2 | 7/2007 |
| WO | 2009012473 A2 | 1/2009 |
| WO | 2009100210 A1 | 8/2009 |
| WO | 2010075445 A1 | 7/2010 |
| WO | 2013008168 A1 | 1/2013 |
| WO | 2013022796 A2 | 2/2013 |
| WO | 2013036193 A1 | 3/2013 |
| WO | 2013130258 A1 | 9/2013 |
| WO | 2013181352 A1 | 12/2013 |
| WO | 2015100178 A1 | 7/2015 |
| WO | 2015134758 A1 | 9/2015 |
| WO | 2016018781 A1 | 2/2016 |
| WO | 2016036660 A1 | 3/2016 |
| WO | 2016164606 A1 | 10/2016 |
| WO | 2016176409 A1 | 11/2016 |
| WO | 2018017981 A1 | 1/2018 |
| WO | 2018156574 A1 | 8/2018 |
| WO | 2019010077 A1 | 1/2019 |
| WO | 2019055487 A1 | 3/2019 |
| WO | 2019173475 A1 | 9/2019 |
| WO | 2019183189 A1 | 9/2019 |
| WO | 2021007200 A1 | 1/2021 |
| WO | 2021087363 A1 | 5/2021 |
| WO | 2021087480 A1 | 5/2021 |
| WO | 2022201081 A1 | 9/2022 |

OTHER PUBLICATIONS

Saint-Gobain Performance Plastics Corporation, "Tygon Medical/Surgical Tubing S-50-HL," pp. 1-2, year 2004.

Silk Road Medical Inc., "Enhance Transcarotid Peripheral Access Kit," pp. 1-2, Dec. 28, 2018.

Silk Road Medical Inc., "Enroute Transcarotid Stent System," pp. 1-4, May 27, 2021.

Sherif, "Homemade TCAR with Flow Reversal for Primary Proximal Carotid Artery Aneurisms in a Patent with Crescendo TIAS post neck operation," Linkedin post, pp. 1-2, year 2021, as downloaded from https://www.linkedin.com/posts/profsherifsultan_nuig-tcar-cast-activity-6710036851517902848-Qwzw.

Silk Road Medical, Inc., "Enroute Transcarotid Neuroprotection System", Manual, pp. 1-20, Mar. 7, 2020, year 2022, as downloaded from file:///C:/Users/Miriam/Downloads/_https__silkroadmed.com_wp-content_uploads_2020_09_11858.7-ENROUTE-NPS-IFU-US-ARTWORK1%20(1).pdf.

Parodi et al., "Cerebral Protection During Carotid Stenting Using Flow Reversal," Journal of Vascular Surgery, vol. 41, No. 3, pp. 416-422, year 2005.

Perez-Grueso et al., "Angioplastia y Stenting Carotideo por Miniacceso Cervical y Flujo Invertido," Angiologia, vol. 56, supl. 1, pp. S225-S234, year 2004.

Luk et al., "Transcarotid Artery Revascularization as a New Modality of Treatment for Carotid Stenosis," Journal Pre-proof, Annals of Vascular Surgery, Elsevier Inc., pp. 1-14, year 2019.

Chang et al., "A New Approach to Carotid Angioplasty and Stenting with Transcervical Occlusion and Protective Shunting: Why it May be a Better Carotid Artery Intervention," Journal of Vascular Surgery, vol. 39, No. 5, pp. 994-1002, May 2004.

Lin et al., "Protected Carotid Artery Stenting and Angioplasty via Transfemoral versus Transcervical Approaches," Vascular and Endovascular Surgery, vol. 39, No. 6, pp. 499-503, year 2005.

Silk Road Medical, "TransCarotid Artery Revascularization (TCAR)," Product Overview, pp. 1-6, year 2022, as downloaded from https://silkroadmed.com/patient-caregivers/the-tcar-procedure/.

Rhodes et al., "Arteriovenous Shunt Measurements in Extremities," Journal of Nuclear Medicine, vol. 13, No. 6, pp. 357-362, year 1972.

"Qosina—Medical Device Components/OEM Components," product catalogue, Qosina Corp., USA, Qosina Europe Srl., Italy, pp. 1-4, year 2022, as downloaded from https://www.qosina.com/.

Sherif, "The TCAR Procedure: Transcervical carotid Artery Revascularization and stenting by C-Guard", Linkedin post, p. 1-1, year 2021, as downloaded from https://www.linkedin.com/feed/update/urn:li: activity:6689646427859140608/.

Drake et al., U.S. Appl. No. 63/211,025, filed Jun. 16, 2021.

InspireMD, "Sustained Embolic Protection", pp. 1-23, Jul. 8, 2020, as downloaded from https://www.inspiremd.com/en/wp-content/uploads/InspireMD-Investor-Deck-Revised-July-8-2020_compressed.pdf.

(56)　　　　　References Cited

OTHER PUBLICATIONS

U.S. Appl. No. 17/576,953 Office Action dated Jul. 20, 2023.
U.S. Appl. No. 18/261,673 Office Action dated Feb. 1, 2024.
CN Application # 2022800098002 Office Action dated Feb. 23, 2024.
JP Applicaton # 2023549856 Office Action dated Mar. 14, 2024.
EP Application # 22739245.3 Search Report dated Apr. 9, 2024.
CN Application # 2022800089963 Office Action dated Apr. 10, 2024.
EP Application # 22774473.7 Search Report dated Jun. 6, 2024.
JP Application # 2023542563 Office Action dated Nov. 21, 2023.
International Application PCT/IB2023/057821 Search report dated Dec. 31, 2023.
Malas et al., "Transcarotid Artery Revascularization versus Transfemoral Carotid Artery Stenting in the Society for Vascular Surgery Vascular Quality Initiative," Journal of Vascular Surgery, vol. 69, No. 1, pp. 92-103, Jan. 2019.
Sultan et al., "Endovascular Management of Saccular Extracranial Internal Carotid Artery Aneurysm using Transcervical Carotid Approach and Flow Reversal," Journal of Vascular Surgery Cases and Innovative Techiques, vol. 5, No. 3, pp. 273-277, year 2019.
Malas et al., "Analysis of the Roadster Pivotal and Extended-access Cohorts Shows Excellent 1-Year Durability of Transcarotid Stenting with Dynamic Flow Reversal," Journal of Vascular Surgery, vol. 69, No. 6, pp. 1786-1796, Jun. 2019.
Elcam Medical, "Y-Click," Product Information, pp. 1-2, Mar. 2024.
"International Standard, ISO 80369-7: Small-bore Connectors for Liquids and Gases in Healthcare Applications—Part 7: Connectors for Intravascular or Hypodermic Applications," First Edition, pp. iv-11, Oct. 15, 2016.
U.S. Appl. No. 18/491,834 Office Action dated Jan. 24, 2025.
Final Office Action, U.S. Appl. No. 18,491,834 dated May 14, 2025.
Non Final Office Action, U.S. Appl. No. 18,491,834, dated Jan. 24, 2025.
Japanese Office Action # 2024-179671, dated Sep. 4, 2025.
Japan Patent Office, Office Action, Application No. 2024-026477, dated Apr. 28, 2025.
Japan Patent Office, Office Action, Application No. 2024-026477, dated Aug. 4, 2025.
World Intellectual Property Organization (WIPO) / Israel Patent Office (ISA/IL), International Search Report and Written Opinion, PCT/IL2025/050040, dated Apr. 30, 2025.
Non-Final Office Action, U.S. Appl. No. 18/571,442, dated Apr. 6, 2026.
Notice of Allowance, U.S. Appl. No. 14/227,585 dated Apr. 14, 2026.
Notice of Appeal from the Examiner, U.S. Appl. No. 17/773,206, dated Mar. 26, 2026.
Notice of Panel Decision from Pre-Appeal Brief Review, U.S. Appl. No. 17/773,206, dated Apr. 27, 2026.

* cited by examiner

INSERT INTO
BLOOD VESSEL

CONNECT TO OTHER
INTRODUCER

DEVICES FOR SHUNTING BLOOD

FIELD OF THE INVENTION

The present invention is related to the field of medical devices, especially devices for shunting blood from an artery to a vein.

BACKGROUND

U.S. Pat. No. 8,545,432 describes a retrograde flow system for treating an artery. The system includes an arterial access device adapted to be introduced into an artery and receive blood flow from the artery. A shunt is fluidly connected to the arterial access device, wherein the shunt provides a pathway for blood to flow from the arterial access device to a return site. A flow control assembly is coupled to the shunt and is adapted to regulate blood flow through the shunt between at least a first blood flow state and at least a second blood flow state. A shut-off valve assembly automatically blocks fluid flow through the shunt in response to injection of the fluid into the arterial access device.

U.S. Pat. No. 7,063,685 describes a hemostasis valve that is closed when not accessed, but which provides an unobstructed fluid pathway when accessed by a luer fitting/connector. An auto-closure valve within the hemostasis valve housing is flush with a top surface thereof. When accessed with a connector or luer fitting, the valve opens completely, allowing an unobstructed high flow fluid path.

SUMMARY OF THE INVENTION

There is provided, in accordance with some embodiments of the present invention, an apparatus including a hub including a front port, a side port, and a back port including a hemostasis valve. The apparatus further includes a sheath extending from the hemostasis valve through the front port and shaped to define one or more lateral openings within the hub. The sheath is configured for insertion into a blood vessel such that, subsequently to the insertion, a rate of flow of blood between the side port and the blood vessel via the lateral openings is controllable using an instrument passing through the hemostasis valve and into the sheath such that the instrument closes at least a portion of the lateral openings.

In some embodiments, a cross-sectional area of a lumen of the side port is at least 3.8 mm$^2$.

In some embodiments, a total area of the lateral openings is at least as large as an area of the side port.

In some embodiments, the sheath includes:
a back sheath, which is disposed within the hub and is shaped to define the lateral openings; and
a front sheath, which is connected to the back sheath and is configured for insertion into the blood vessel.

In some embodiments, the sheath is connected to the back port.

In some embodiments, the apparatus further includes a tube configured to connect to the side port.

In some embodiments, the apparatus further includes the instrument.

In some embodiments, the instrument includes a dilator configured to facilitate the insertion by dilating the blood vessel.

In some embodiments, the instrument includes one or more markings configured to indicate a size of the portion of the lateral openings that is closed by the instrument, by virtue of the markings progressively entering the hub as the instrument is pushed through the hemostasis valve.

In some embodiments, the openings are arranged in one or more rows.

In some embodiments, the openings include one or more slots.

In some embodiments, the apparatus further includes a blood filter disposed between the lateral openings and the side port such that the blood flows through the blood filter.

There is further provided, in accordance with some embodiments of the present invention, a method including inserting a sheath, which extends from a hemostasis valve at a back port of a hub through a front port of the hub, into a blood vessel, the sheath being shaped to define one or more lateral openings within the hub. The method further includes, subsequently to inserting the sheath, controlling a rate of flow of blood between a side port of the hub and the blood vessel via the lateral openings, by passing an instrument through the hemostasis valve and into the sheath such that the instrument closes at least a portion of the lateral openings.

There is further provided, in accordance with some embodiments of the present invention, a kit for use with a hub including a front port, which is connected to a sheath, and a back port, which includes a hemostasis valve. The kit includes a tube, and an adapter configured to connect to the tube and configured for insertion through the hemostasis valve such that, subsequently to an insertion of the sheath into a blood vessel, blood flows between the blood vessel and the tube via the adapter.

In some embodiments, the adapter includes one or more barbs configured to inhibit the adapter from exiting the hub subsequently to the insertion of the adapter.

In some embodiments, the adapter includes:
a straight connector, including:
a front end, configured for insertion through the hemostasis valve; and
a back end; and
a tube connector, which includes a front port connected to the back end of the straight connector and is configured to connect to the tube.

In some embodiments, the tube connector further includes a back port configured to connect to the tube.

In some embodiments, the tube connector further includes:
a back port, including another hemostasis valve; and
one or more side ports, at least one of which is configured to connect to the tube.

In some embodiments, the tube connector includes a T-connector.

In some embodiments, the tube connector includes a Y-connector.

In some embodiments, the kit further includes another adapter configured for insertion into another hub connected to another sheath configured for insertion into another blood vessel.

In some embodiments, the kit further includes:
another hub including another front port, a side port, and another back port including another hemostasis valve; and
another sheath extending from the other hemostasis valve through the other front port and shaped to define one or more lateral openings within the other hub,
the other sheath being configured for insertion into another blood vessel such that, subsequently to the insertion, a rate of flow of the blood between the side port and the other blood vessel via the lateral openings is controllable using an instrument passing through the other hemostasis valve and into the other sheath such that the instrument closes at least a portion of the lateral openings.

There is further provided, in accordance with some embodiments of the present invention, an apparatus including a sheath. The apparatus further includes a hub, including a front port, which is connected to the sheath, and a back port including a hemostasis valve. The apparatus further includes an adapter passing through the hemostasis valve and a tube connected to the adapter such that, subsequently to an insertion of the sheath into a blood vessel, blood flows between the blood vessel and the tube via the adapter.

There is further provided, in accordance with some embodiments of the present invention, a method including inserting an adapter, which is connected to a tube, through a hemostasis valve at a back port of a hub. The method further includes inserting a sheath, which is connected to a front port of the hub, into a blood vessel such that blood flows between the blood vessel and the tube via the adapter.

In some embodiments, the adapter is a first adapter, the hub is a first hub, the hemostasis valve is a first hemostasis valve, the sheath is a first sheath, and the blood vessel is a first blood vessel, and the method further includes:

inserting a second adapter through a second hemostasis valve at a back port of a second hub;

inserting a second sheath, which is connected to a front port of the second hub, into a second blood vessel; and connecting the tube to the second hub such that the blood flows between the first blood vessel and the second blood vessel via the tube.

In some embodiments, connecting the tube to the second hub includes connecting the tube to the second hub via a device configured to perform a function selected from the group of functions consisting of: filtering the blood, indicating a flow rate of the blood, and facilitating control of the flow rate.

In some embodiments, the hub is a first hub, the hemostasis valve is a first hemostasis valve, the sheath is a first sheath, and the blood vessel is a first blood vessel, and the method further includes:

inserting a second sheath, which extends from a second hemostasis valve at a back port of a second hub through a front port of the second hub, into a second blood vessel, the sheath being shaped to define one or more lateral openings within the second hub; and connecting the tube to the second hub such that the blood flows between the first blood vessel and the second blood vessel via the tube and the lateral openings.

The present invention will be more fully understood from the following detailed description of embodiments thereof, taken together with the drawings, in which:

4

Figures 2A, 2B, 3:
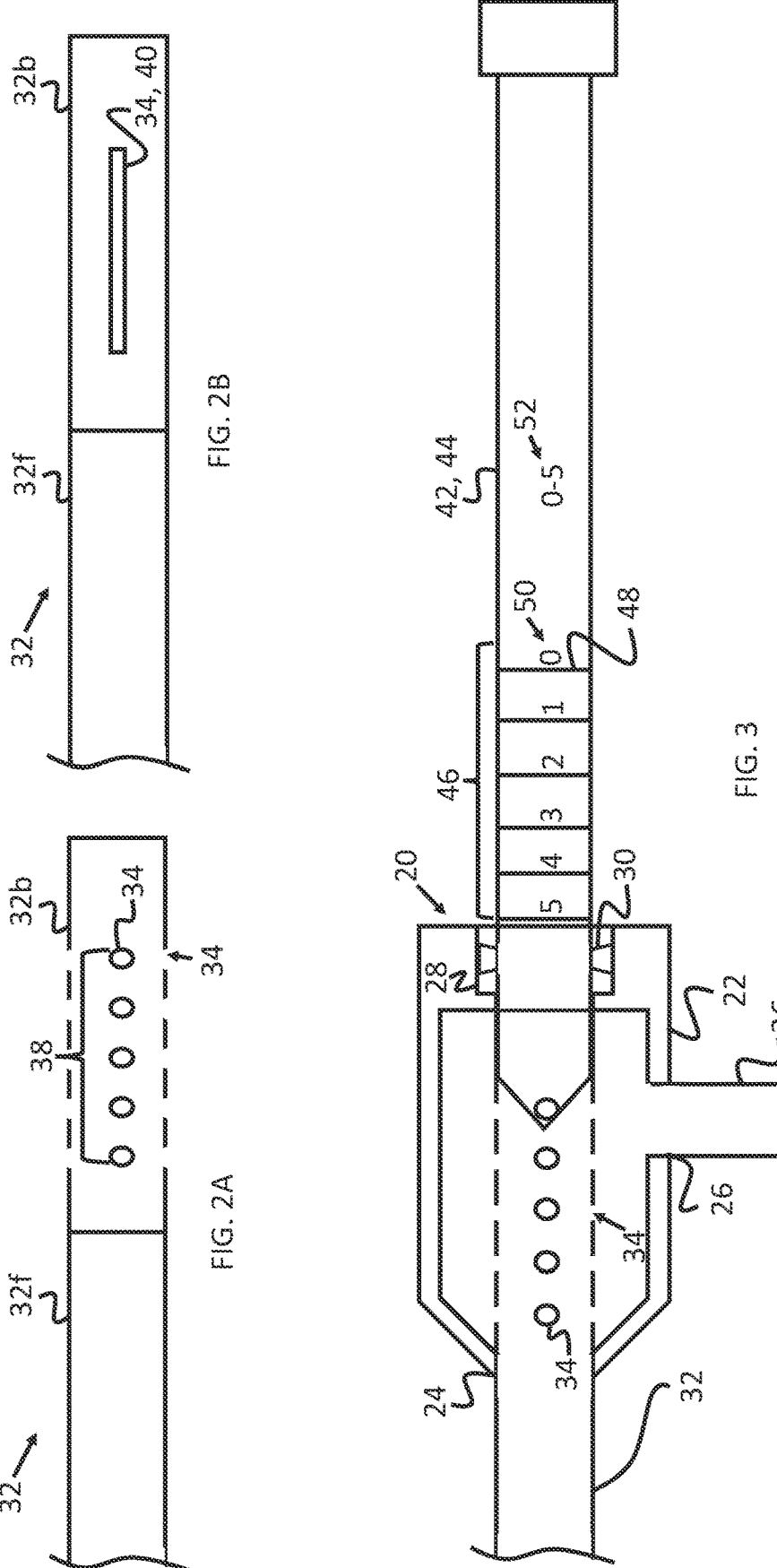
Figures 4, 5A, 5B:
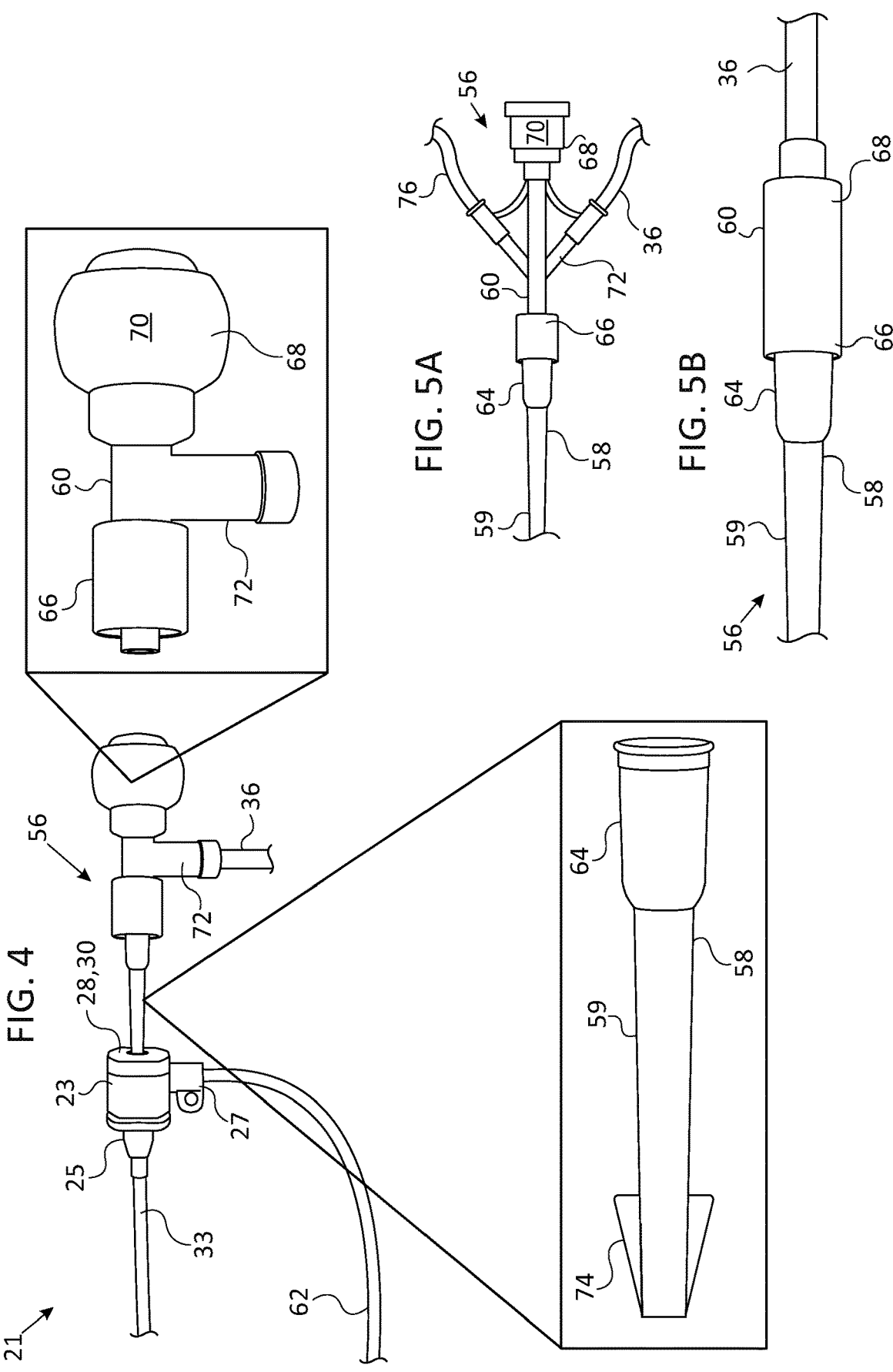
Figure 6A:
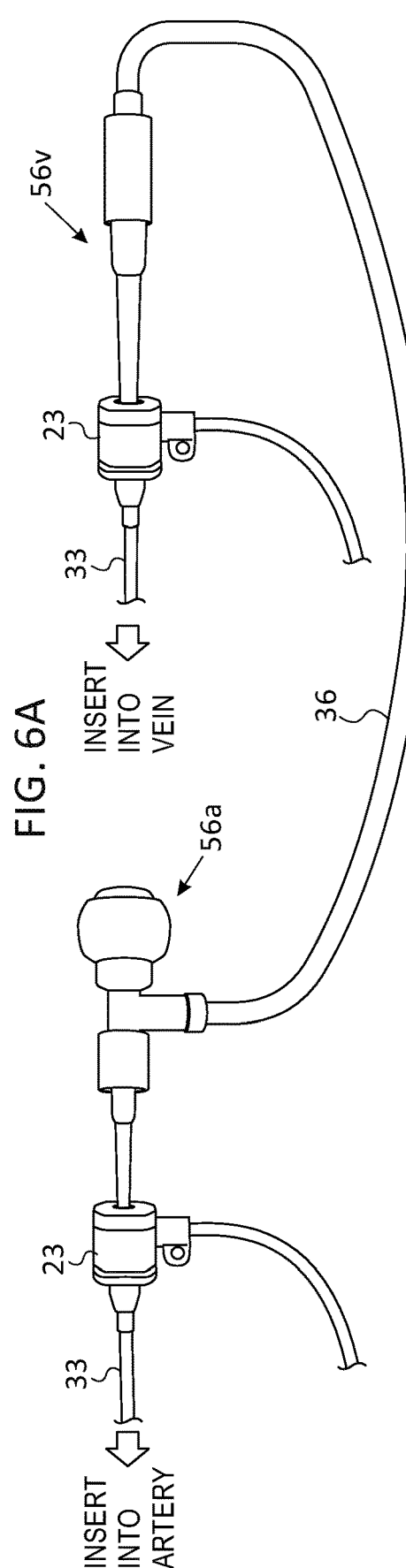
Figure 6B:
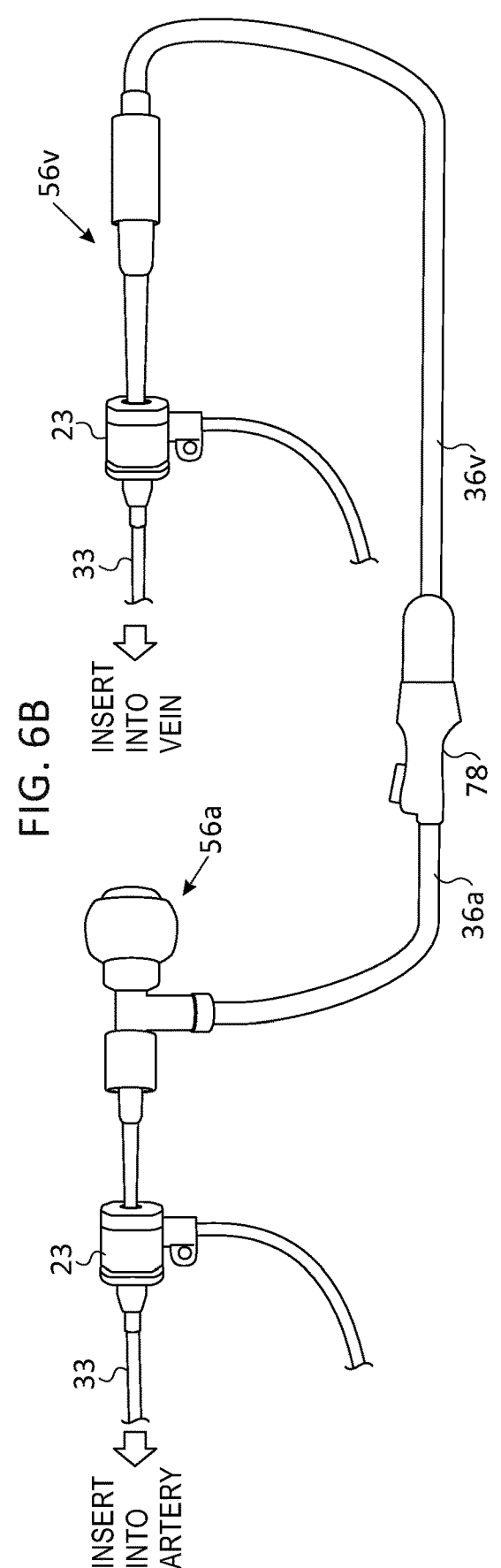
Figures 6C, 7:
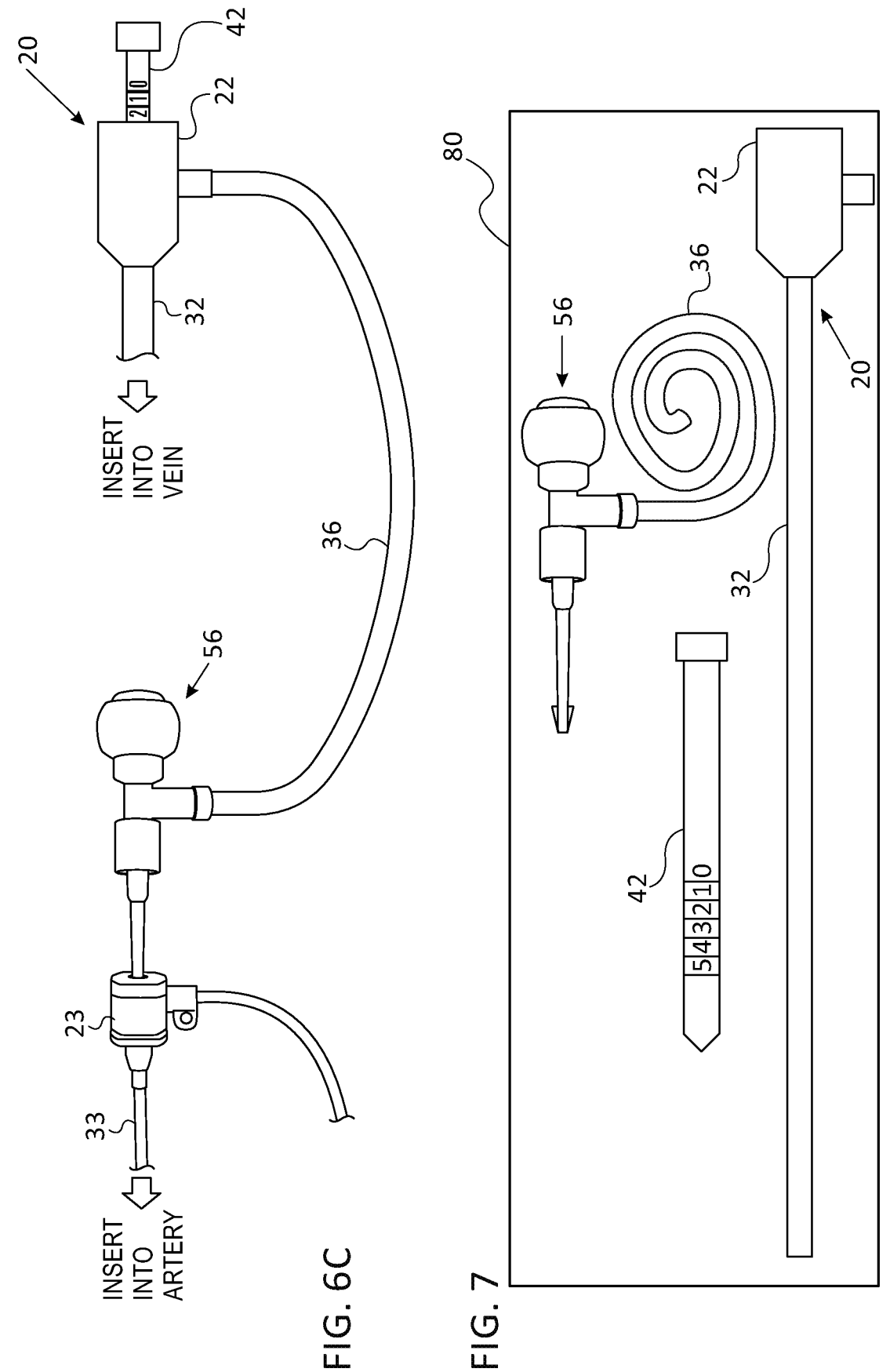

FIGS. 2A-B are schematic illustrations of a sheath, in accordance with some embodiments of the present invention;

FIG. 3 is a schematic illustration of a technique for controlling a rate of blood flow through a hub, in accordance with some embodiments of the present invention;

FIG. 4 is a schematic illustration of an introducer apparatus, in accordance with some embodiments of the present invention;

FIGS. 5A-B are schematic illustrations of an adapter connected to a tube, in accordance with some embodiments of the present invention;

FIGS. 6A-C are schematic illustrations of techniques for shunting blood, in accordance with some embodiments of the present invention; and FIG. 7 is a schematic illustration of a kit for use with a conventional introducer hub, in accordance with some embodiments of the present invention.

DETAILED DESCRIPTION OF EMBODIMENTS

Overview

In some procedures, an introducer apparatus, also referred to herein simply as an "introducer," provides access to a blood vessel of a subject. An introducer comprises a sheath connected to an introducer hub. Optionally, following the percutaneous insertion of the sheath into the blood vessel, other tools and devices may be passed through the sheath and into the blood vessel via the hub.

During a procedure to clear an occlusive lesion from an artery, such as a carotid artery, the flow of blood toward the lesion may be stopped so as to prevent any emboli from being carried downstream. While the downstream flow through the artery is stopped, blood reaching the area of the lesion via other arteries may be diverted through the sheath and introducer hub, such that any debris generated by the procedure may be safely removed from the subject's body. To prevent an excessive loss of blood, the blood may be shunted, through a filter, to a vein of the subject. For example, the blood may be shunted to a femoral, radial, or jugular vein.

In a conventional introducer, a front port of the hub is connected to the back end of the sheath, and a side port of the hub is connected to a tube via which the blood may be shunted. While the blood flows through the side port, a guidewire, a stent, and/or any other tool or device may be passed through a back port of the hub, which typically comprises a hemostasis valve.

One challenge with conventional introducers is that the rate of blood flow through the hub cannot be controlled.

To address this challenge, embodiments of the present invention provide an improved introducer, which may be used at either the arterial side or the venous side of a shunt. In this introducer, the sheath does not terminate at the front port of the hub, but rather, extends through the hub to the back port of the hub. The portion of the sheath inside the hub is shaped to define one or more lateral openings through which the blood may flow. By inserting an instrument, such as a dilator or an obturator, through the back port of the hub and into the sheath, the openings may be selectively occluded, thereby reducing the flow rate of the blood. Advantageously, the instrument may comprise markings that indicate, to the physician, the extent to which the openings are occluded.

Another challenge with conventional introducers is that the rate of blood flow may be restricted by the relatively small lumen of the side port.

The improved introducer described above may address this challenge by providing a side port having a widened lumen.

In addition, embodiments of the present invention provide an adapter configured to increase the flow rate through a conventional hub. The adapter is inserted through the hemostasis valve of the back port of the hub, and a tube for blood flow is connected to the adapter. The adapter thus facilitates using the wider back port of the hub, rather than the side port, for blood flow.

The adapter may be used at either the arterial side or the venous side of a shunt. At the arterial side, the adapter typically comprises one or more side ports, one of which is connected to the tube, and the back port of the adapter is used for the passage of tools and devices. At the venous side, the tube may be connected to the back port of the adapter, and the adapter need not necessarily comprise any side ports.

Introducer with Flow-Rate Control

Figure 1B:
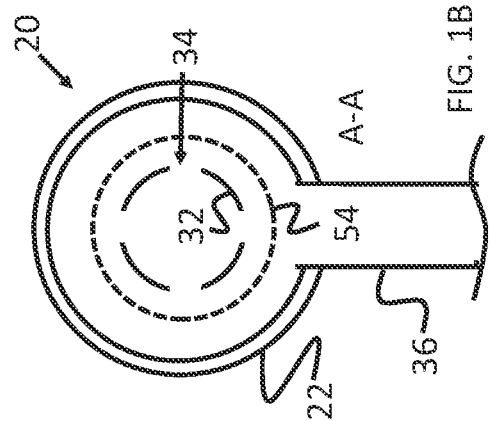
FIG. 1B is a schematic illustration of a cross-section through the introducer apparatus of FIG. 1A, in accordance with some embodiments of the present invention.
Figure 1A:
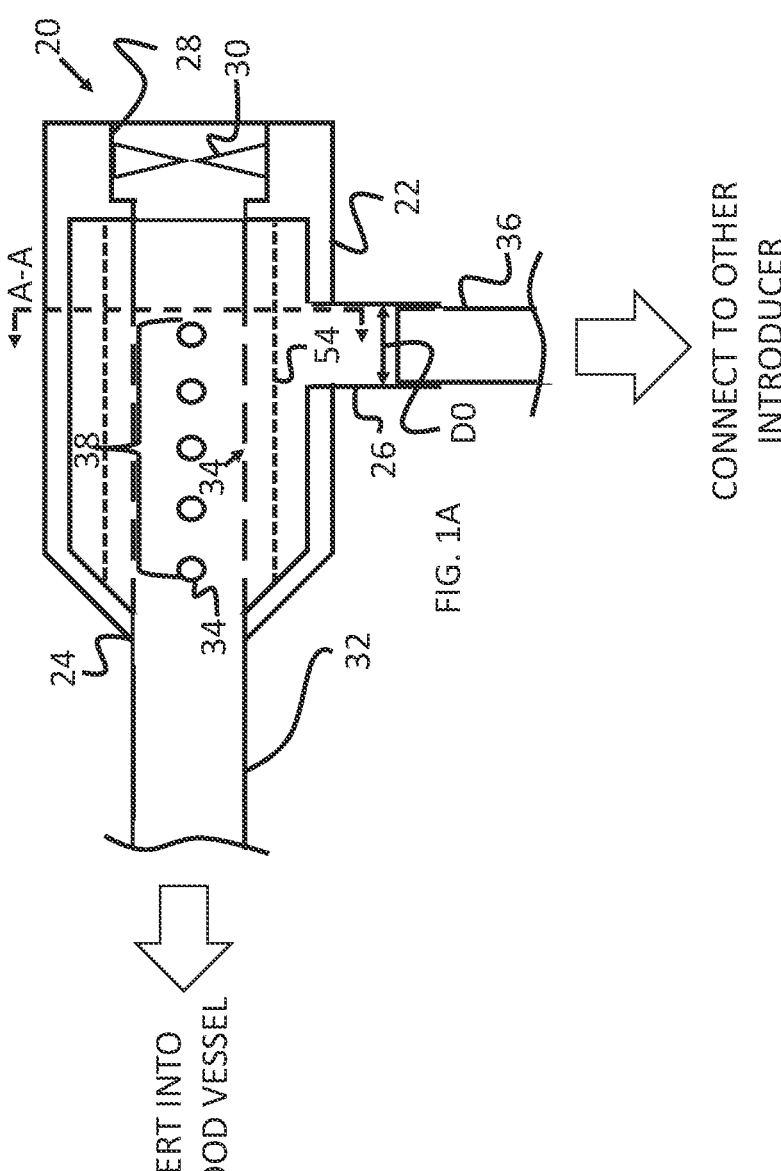
FIG. 1A is a schematic illustration of an introducer apparatus, in accordance with some embodiments of the present invention.

Reference is initially made to FIG. 1A, which is a schematic illustration of an introducer apparatus 20, in accordance with some embodiments of the present invention. Reference is further made to FIG. 1B, which is a schematic illustration of a cross-section A-A through apparatus 20, in accordance with some embodiments of the present invention.

Apparatus 20 comprises a hub 22 comprising a front port 24, a side port 26, and a back port 28 comprising a hemostasis valve 30. Each of the ports may comprise a protrusion from the body of the hub as in the case of side port 26 in FIG. 1A, a chamber recessed within the body of the hub as in the case of back port 28 in FIG. 1A, or a simple opening as in the case of front port 24 in FIG. 1A.

Apparatus 20 further comprises a sheath 32 extending from the hemostasis valve through the front port and shaped to define one or more lateral openings 34 within hub 22. For example, for each opening 34, a vector normal to the opening may be perpendicular to the longitudinal axis of sheath 32 at the opening. Sheath 32 may have any suitable diameter, such as 6-18 Fr. Typically, the back end of sheath 32 is bonded to back port 28.

Sheath 32 is configured for insertion into a blood vessel. As further described below with reference to FIG. 3, subsequently to the insertion of the sheath into the blood vessel, the rate of flow of blood between side port 26 and the blood vessel via openings 34 may be controlled using an instrument passing through hemostasis valve 30 and into the sheath such that the instrument closes at least a portion of the openings.

Typically, the cross-sectional area of the lumen of side port 26 is larger than in a conventional introducer. For example, the inner diameter DO of the side port may be at least 2 mm and/or the cross-sectional area of the lumen may be at least 3.1 mm$^2$.

Typically, the total area of openings 34 is at least as large as the cross-sectional area of the side-port lumen, such that the rate of blood flow is not limited by the openings. For example, the total area of the openings may be 20-100% greater than the area of the side-port lumen. As a specific example, the area of the side-port lumen may be 4 mm$^2$, and the total area of the openings may be 5-8 mm$^2$.

Typically, during a procedure on an artery, the sheath is inserted into a vein so as to facilitate the shunting of blood from the artery to the vein. As a specific example, during a procedure on a carotid artery, the sheath may be inserted into a femoral, radial, or jugular vein so as to facilitate the shunting of blood from the carotid artery to the vein.

In other embodiments, the sheath is inserted into the artery. In such embodiments, a separate, conventional introducer may be used to introduce tools into the artery, such that back port 28 of apparatus 20 may be reserved for controlling the rate of blood flow.

Typically, apparatus 20 further comprises a tube 36 configured to connect to side port 26. For example, tube 36 may be permanently connected to the side port, e.g., by virtue of being bonded to the inner or outer wall of the side port. Alternatively, the tube may be configured to reversibly connect to the side port, e.g., via a Luer-lock connection.

Tube 36 is configured to carry blood to or from hub 22.

For example, for embodiments in which sheath 32 is inserted into a vein, tube 36 may be connected to another introducer apparatus comprising another sheath inserted into an artery, such that the tube carries blood from the artery to hub 22. (An example of such embodiments is described below with reference to FIG. 6C.) Alternatively, for embodiments in which sheath 32 is inserted into an artery, tube 36 may be connected to another introducer apparatus comprising another sheath inserted into a vein, such that the tube carries blood from the hub to the vein. In each of the examples above, the tube may be connected to the other introducer directly or via another tube, and the connection may be permanent or reversible.

Alternatively, tube 36 may carry blood from the hub to a collection bag.

In some embodiments, apparatus 20 further comprises a blood filter 54 disposed between the lateral openings and the side port such that the blood flows through blood filter 54. For example, hub 22 may contain a cylindrical blood filter 54 that surrounds sheath 32.

Alternatively or additionally, side port 26 may contain a blood filter.

In some embodiments, at least a portion of hub 22 is transparent. One or more moveable objects, such as beads, are disposed within the hub such that the moveable objects may be viewed through the transparent portion of the hub. The moveable objects are configured to move in response to the flow of blood through the hub, thereby indicating the flow to the physician. The moveable objects may have any of the features described in U.S. patent application Ser. No. 17/576,953, whose disclosure is incorporated herein by reference.

Reference is now additionally made to FIGS. 2A-B, which are schematic illustrations of sheath 32, in accordance with some embodiments of the present invention.

In some embodiments, openings 34 are arranged in one or more rows 38, such as multiple rows 38 distributed around the circumference of sheath 32. For example, as shown in FIGS. 1A and 2A, openings 34 may be arranged in four rows distributed around the circumference of the sheath. Each row may include any number of openings, such as between two and ten openings.

In such embodiments, openings 34 may be circular or may have any other suitable shape.

Alternatively or additionally, as shown in FIG. 2B, the openings may include one or more slots 40, such as multiple (e.g., four) slots 40 distributed around the circumference of sheath 32. Typically, in such embodiments, the longitudinal axis of each slot is parallel to the longitudinal axis of the sheath at the slot.

In some embodiments, as shown in FIGS. 2A-B, sheath 32 comprises a back sheath 32b, which is disposed within hub 22 and is shaped to define openings 34, and a front sheath 32f. Front sheath 32f is connected (e.g., bonded) to back sheath 32b; in particular, the back end of the front sheath is connected to the front end of the back sheath, such that blood may flow between the front sheath and the back sheath. The front sheath, which is typically more flexible than the back sheath, is configured for insertion into the blood vessel.

In some embodiments, hub 22 is manufactured by molding a polymer such as acrylonitrile butadiene styrene (ABS) or a polycarbonate. In such embodiments, back sheath 32b may be molded together with the hub, such that the back sheath is integral with the hub. Alternatively, regardless of the material from which the hub is manufactured and regardless of the technique used to manufacture the hub, back sheath 32b—or the entire sheath, for embodiments in which the sheath does not comprise connected front and back sections—may be manufactured separately from the hub and then connected (e.g., bonded) to back port 28. For example, back sheath 32b may be manufactured by extruding a polymer such as polyethylene or polyether block amide (PEBA) and then forming openings 34 in the extrusion.

Reference is now made to FIG. 3, which is a schematic illustration of a technique for controlling a rate of blood flow through hub 22, in accordance with some embodiments of the present invention.

To control the rate of flow between side port 26 and the blood vessel into which sheath 32 is inserted, an instrument 42 is passed through hemostasis valve 30. As instrument 42 is passed further into the sheath, the instrument occludes more of openings 34, thereby restricting blow flow between the side port and the sheath. Conversely, as the instrument is withdrawn, more of the openings are opened, such that the flow rate through the openings is increased. In some embodiments, instrument 42 is provided, together with the other components of apparatus 20, in a kit.

Typically, to facilitate controlling the rate of blood flow between the side port and the sheath as described above, the outer diameter of the instrument is approximately the same as the inner diameter of sheath 32.

In some embodiments, instrument 42 comprises a dilator 44 configured to facilitate the insertion of the sheath into the blood vessel by dilating the blood vessel. In other words, subsequently to dilating the blood vessel, dilator 44 may be used to control the flow rate. For example, the dilator may be passed through the sheath, via back port 28 and hemostasis valve 30, until the dilator punctures the blood vessel. Subsequently, the dilator may be withdrawn until at least a portion of openings 34 is not occluded. Subsequently, the dilator may be further withdrawn or advanced so as to control the flow rate through openings 34.

In other embodiments, a separate instrument 42 is used. For example, after completely withdrawing the dilator from the hub, an obturator—which is shorter, and thus easier to use, than the dilator—may be inserted into the hub and used for flow control.

Typically, instrument 42 comprises one or more markings 46 configured to indicate the size of the portion of the lateral openings that is closed by the instrument, by virtue of markings 46 progressively entering the hub as the instrument is pushed through the hemostasis valve. In other words, the markings are placed such that when the openings are not occluded at all, all the markings are outside the hub, but as the occlusion is increased, more of the markings enter the hub. Thus, the physician may readily ascertain the extent of the occlusion based on the extent to which the markings are visible.

For example, markings 46 may comprise a series of arcs 48 placed at different respective positions along the longitudinal axis of the instrument, such that the number of visible arcs 48 indicates the extent to which the openings are occluded. (Each arc 48 may be closed, thus defining a circle.) For embodiments in which openings 34 are arranged in rows, the arcs may be placed such that the number of visible arcs equals the number of openings in each row that are not occluded by the instrument.

Alternatively or additionally to arcs 48, markings 46 may comprise alphanumeric markings, such as numbers 50, such that the frontmost visible marking indicates the amount of occlusion. For embodiments in which openings 34 are arranged in rows, the frontmost visible marking may indicate the number of openings in each row that are not occluded by the instrument.

In some embodiments, a scale 52, which facilitates interpreting the markings, is also marked on the instrument. For example, for embodiments in which the markings comprise numbers 50, scale 52 may include the minimum and maximum number separated by a hyphen from one another.

Adapter for Increased Flow Rate

Reference is now made to FIG. 4, which is a schematic illustration of a conventional introducer apparatus 21 with an adapter 56, in accordance with some embodiments of the present invention. Reference is further made to FIGS. 5A-B, which are schematic illustrations of an adapter 56 connected to tube 36, in accordance with some embodiments of the present invention.

Apparatus 21 comprises a hub 23 and a sheath 33, which have conventional features and are connected to one another in a conventional way. In particular, sheath 33 is not shaped to define any lateral openings and does not pass through hub 23; rather, sheath 33 is connected to a front port 25 of the hub.

Adapter 56 is configured to facilitate the flow of blood between hub 23 and tube 36 via back port 28 of the hub. In particular, the adapter is configured to connect permanently or reversibly to the tube and is configured for insertion through hemostasis valve 30 such that, subsequently to the insertion of sheath 33 into a blood vessel, blood flows between the blood vessel and tube 36 via the adapter. Typically, to facilitate this flow, the diameter of the lumen of adapter 56 at the narrowest portion of the lumen is at least 2 mm.

Typically, adapter 56 comprises a straight connector 58 and a tube connector 60, which is configured to connect to tube 36. Straight connector 58 comprises a front end 59, configured for insertion through the hemostasis valve of hub 23, and a back end 64. Tube connector 60 comprises a front port 66 connected to back end 64. Typically, tube connector 60 further comprises a back port 68.

Typically, front port 66 is connected to back end 64 via a Luer-lock connection. For example, front port 66 may comprise a male Luer lock, and back end 64 may comprise a female Luer lock connected to the male Luer lock. Alternatively, front port 66 may be bonded to back end 64.

In other embodiments, adapter 56 is manufactured as a single integrated connector, which may comprise features of straight connector 58 and tube connector 60.

In some embodiments, as shown in FIG. 5B, back port 68 is configured to connect to tube 36, e.g., by virtue of being bonded or Luer-locked to the tube. Typically, in such embodiments, the tube connector does not comprise any side ports, and sheath 33 is inserted into a vein.

In other embodiments, as shown in FIGS. 4 and SA, tube connector 60 comprises one or more side ports 72, at least one of which is configured to connect to tube 36, e.g., by virtue of being bonded or Luer-locked to the tube. (Optionally, the side port may connect to the tube via an aspiration port.) Typically, in such embodiments, back port 68 comprises another hemostasis valve 70, and sheath 33 is inserted into an artery. A guidewire, a catheter, a stent, and/or any other tool or device may be passed through back port 68.

For example, as shown in FIG. 4, the tube connector may comprise a T-connector, which comprises a single side port 72 perpendicular to the axis passing between front port 66 and back port 68.

Alternatively, as shown in FIG. 5A, the tube connector may comprise a Y-connector, which comprises one or more side ports 72 at an oblique angle with respect to the axis passing between front port 66 and back port 68. For example, the Y-connector may comprise two side ports. One of the side ports may be connected to tube 36, and the other side port may be connected to another tube 76. Saline, contrast material, and/or any other fluid may be inserted into the blood vessel via tube 76.

As yet another alternative, the tube connector may comprise a series of two T-connectors or two Y-connectors, or a Y-connector connected to a T-connector. Typically, in such embodiments, the back port of the front member of the series comprises a Luer lock for locking to the back member of the series, while the back port of the back member of the series comprises hemostasis valve 70.

In some embodiments, adapter 56 comprises one or more barbs 74 configured to inhibit the adapter from exiting hub 23 subsequently to the insertion of the adapter into the hub. For example, as shown in FIG. 4, for embodiments in which the adapter comprises straight connector 58, the straight connector may comprise barbs 74. Each barb 74 is shaped such that the barb generates relatively little resistance when passed forward through hemostasis valve 30 but significant resistance when pulled backward. For example, each barb may comprise a triangular protrusion that is wider at the back than at the front, such that the valve resists the backward sliding of the protrusion therethrough.

In some embodiments, another tube 62 is connected to a side port 27 of the hub. Saline, contrast material, and/or any other fluid may be inserted into the blood vessel via tube 62.

Reference is now made to FIGS. 6A-C, which are schematic illustrations of techniques for shunting blood, in accordance with some embodiments of the present invention.

As described above with reference to FIG. 1A, tube 36 may facilitate shunting blood between two blood vessels.

For example, one adapter 56 may be inserted into a first introducer inserted into a first blood vessel, and another adapter may be inserted into a second introducer inserted into a second blood vessel. Blood may then flow between the two blood vessels via tube 36.

As a specific example, as shown in FIG. 6A, tube 36 may connect at one end to an arterial-side adapter 56a, comprising the adapter of FIG. 4 or FIG. 5A for example, and at the other end to a venous-side adapter 56v, comprising the adapter of FIG. 5B for example. Alternatively, as shown in FIG. 6B, the two adapters may be connected to one another via a device 78 for filtering the blood, indicating the rate of blood flow, and/or controlling the rate of blood flow. In particular, arterial-side adapter 56a may be connected directly or via an arterial-side tube 36a to the inlet port of device 78, and venous-side adapter 56v may be connected directly or via an venous-side tube 36v to the outlet port of device 78. (Each connection may be permanent, e.g., via bonding, or reversible, e.g., via a Luer lock.) Example embodiments of device 78 are described, for example, in International Application PCT/IB2022/052688 and U.S. patent application Ser. No. 17/576,953, whose respective disclosures are incorporated herein by reference.

Alternatively, as shown in FIG. 6C, an adapter 56 and an introducer apparatus 20 may be connected to one another via tube 36. An advantage of such embodiments is that adapter 56 and the widened side port of apparatus 20 facilitate an increased flow rate, yet the flow rate can be reduced, if necessary, using instrument 42. Typically, in such embodiments, adapter 56 is inserted into an arterial-side introducer, and sheath 32 of apparatus 20 is inserted into a vein.

Alternatively to facilitating the shunting of blood, tube 36 may carry blood from an arterial-side adapter to a collection bag.

Reference is now made to FIG. 7, which is a schematic illustration of a kit for use with a conventional introducer hub, in accordance with some embodiments of the present invention.

Typically, an arterial-side adapter and/or a venous-side adapter is provided, together with tube 36, in a kit 80. (The tube may be preconnected to at least one of the adapters.) Kit 80 may further comprise additional components such as apparatus 20, instrument 42, device 78 (FIG. 6B), and/or a conventional introducer. Thus, advantageously, kit 80 may facilitate implementing any suitable shunting technique, such as any of the techniques illustrated in FIGS. 6A-C.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   a hub comprising a front port, a side port, and a back port comprising a hemostasis valve;
   a sheath extending from the hemostasis valve through the front port and shaped to define one or more lateral openings within the hub,
   the sheath being configured for insertion into a blood vessel; and
   an instrument configured to reduce a rate of flow of blood between the side port and the blood vessel via the lateral openings without stopping the flow, subsequently to the insertion, by passing through the hemostasis valve and into the sheath such that the instrument closes at least a portion of the lateral openings.

2. The apparatus according to claim 1, wherein a cross-sectional area of a lumen of the side port is at least 3.8 mm$^2$.

3. The apparatus according to claim 1, wherein a total area of the lateral openings is at least as large as an area of the side port.

4. The apparatus according to claim 1, wherein the sheath comprises:

a back sheath, which is disposed within the hub and is shaped to define the lateral openings; and a front sheath, which is connected to the back sheath and is configured for insertion into the blood vessel.

5. The apparatus according to claim 1, wherein the sheath is connected to the back port.

6. The apparatus according to claim 1, further comprising a tube configured to connect to the side port.

7. The apparatus according to claim 1, wherein the instrument comprises a dilator configured to facilitate the insertion by dilating the blood vessel.

8. The apparatus according to claim 1, wherein the openings are arranged in one or more rows.

9. The apparatus according to claim 1, wherein the openings include one or more slots.

10. The apparatus according to claim 1, further comprising a blood filter disposed between the lateral openings and the side port such that the blood flows through the blood filter.

11. The apparatus according to claim 1, wherein the apparatus is for use with another hub including another front port, which is connected to another sheath, and another back port, which includes another hemostasis valve, and wherein the apparatus further comprises:

a tube configured to connect to the side port; and an adapter configured to connect to the tube and configured for insertion through the other hemostasis valve such that, subsequently to an insertion of the other sheath into another blood vessel, the blood flows between the other blood vessel and the tube via the adapter.

12. The apparatus according to claim 11, wherein the adapter comprises one or more barbs configured to inhibit the adapter from exiting the other hub subsequently to the insertion of the adapter.

13. The apparatus according to claim 11, wherein the adapter comprises:

a straight connector, comprising:

a front end, configured for insertion through the other hemostasis valve; and a back end; and a tube connector, which comprises a front connector port connected to the back end of the straight connector and is configured to connect to the tube.

14. The apparatus according to claim 13, wherein the tube connector further comprises a back connector port configured to connect to the tube.

15. The apparatus according to claim 13, wherein the other hemostasis valve is a first other hemostasis valve, and wherein the tube connector further comprises:

a back connector port, comprising a second other hemostasis valve; and one or more side connector ports, at least one of which is configured to connect to the tube.

16. The apparatus according to claim 13, wherein the tube connector comprises a T-connector.

17. The apparatus according to claim 13, wherein the tube connector comprises a Y-connector.

18. The apparatus according to claim 1, further comprising:

another sheath;

another hub, comprising another front port, which is connected to the other sheath, and another back port comprising another hemostasis valve;

an adapter passing through the other hemostasis valve; and a tube configured to connect to the side port and connected to the adapter such that, subsequently to an insertion of the other sheath into another blood vessel, the blood flows between the other blood vessel and the tube via the adapter.

19. The apparatus according to claim 1, wherein the instrument comprises multiple markings configured to indicate different respective sizes of the portion of the lateral openings that is closed by the instrument, by virtue of the markings progressively entering the hub as the instrument is pushed through the hemostasis valve.

20. A method, comprising:

inserting a sheath, which extends from a hemostasis valve at a back port of a hub through a front port of the hub, into a blood vessel, the sheath being shaped to define one or more lateral openings within the hub; and subsequently to inserting the sheath, passing an instrument through the hemostasis valve and into the sheath, and using the instrument to close at least a portion of the lateral openings so as to control a rate of flow of blood between a side port of the hub and the blood vessel via the lateral openings.

21. The method according to claim 20, further comprising:

inserting an adapter, which is connected to a tube connected to the side port, through another hemostasis valve at another back port of another hub; and inserting another sheath, which is connected to another front port of the other hub, into another blood vessel such that the blood flows between the other blood vessel and the tube via the adapter.

22. The method according to claim 20, wherein using the instrument comprises using the instrument to reduce the rate without stopping the flow, by closing the portion of the lateral openings.

\*   \*   \*   \*   \*